United States Patent [19]
Spery

[11] Patent Number: 5,433,219
[45] Date of Patent: Jul. 18, 1995

[54] RECEPTIVE CONDOM ASSEMBLY

[76] Inventor: Nanette S. Spery, 880 W. 181st St., New York, N.Y. 10033

[21] Appl. No.: 950,418

[22] Filed: Sep. 23, 1992

[51] Int. Cl.⁶ .......................... A61F 6/04; A61F 13/15
[52] U.S. Cl. .................................... 128/844; 128/918; 604/364
[58] Field of Search ................. 128/842, 844, 830–840, 128/918; 604/364, 330, 347–353

[56] References Cited

U.S. PATENT DOCUMENTS

| | | |
|---|---|---|
| 2,267,030 | 12/1941 | Hill ..................................... 128/285 |
| 3,128,762 | 4/1964 | Young . |
| 3,130,721 | 4/1964 | Young . |
| 3,452,749 | 7/1969 | Riedell . |
| 3,464,409 | 9/1969 | Murphy . |
| 3,495,589 | 2/1970 | Clement . |
| 3,512,528 | 5/1970 | Whitehead et al. . |
| 3,553,308 | 1/1971 | Kobayashi et al. . |
| 3,563,244 | 2/1971 | Asaka et al. . |
| 3,590,816 | 7/1971 | Rosenthal . |
| 3,639,600 | 2/1972 | Hendrix . |
| 3,640,284 | 2/1972 | De Langis . |
| 3,690,310 | 9/1972 | Mintz . |
| 3,712,910 | 1/1973 | Anachenko et al. . |
| 3,749,096 | 7/1973 | Donaldson . |
| 3,758,687 | 9/1973 | Kimble et al. . |
| 3,822,355 | 7/1974 | Kincl . |
| 3,836,651 | 9/1974 | Kincl et al. . |
| 3,854,475 | 12/1974 | Bucalo . |
| 3,921,311 | 11/1975 | Beasley et al. . |
| 3,932,635 | 1/1976 | Segre . |
| 3,939,264 | 2/1976 | Lachnit-Fixson . |
| 3,942,641 | 3/1976 | Segre . |
| 3,969,502 | 7/1976 | Lachnit-Fixson . |
| 4,009,717 | 3/1977 | Allen . |
| 4,018,919 | 4/1977 | Black . |
| 4,029,779 | 6/1977 | Elger et al. . |
| 4,066,757 | 1/1978 | Pasquale . |
| 4,098,905 | 7/1978 | Blake et al. . |
| 4,100,309 | 7/1978 | Micklus et al. . |
| 4,102,998 | 7/1978 | Gutnick . |
| 4,119,094 | 10/1978 | Micklus et al. . |
| 4,122,166 | 10/1978 | Stagg et al. . |
| 4,123,519 | 10/1978 | Stagg et al. . |
| 4,143,136 | 3/1979 | De Jage et al. . |
| 4,144,334 | 3/1979 | Elger et al. . |
| 4,171,358 | 10/1979 | Black . |
| 4,186,742 | 2/1980 | Donald . |
| 4,198,976 | 4/1980 | Drobish et al. . |
| 4,200,091 | 4/1980 | Del Conte . |
| 4,219,016 | 8/1980 | Drobish et al. . |
| 4,232,675 | 11/1980 | Meldahl . |
| 4,247,552 | 1/1981 | Hallesy et al. . |
| 4,252,787 | 2/1981 | Jacobson et al. . |
| 4,253,997 | 3/1981 | Sarantakis . |
| 4,263,282 | 4/1981 | Von Der Ohe et al. . |
| 4,275,812 | 6/1981 | Poncy et al. . |
| 4,277,475 | 7/1981 | Vickery . |
| 4,281,648 | 8/1981 | Rogers . |
| 4,297,343 | 10/1981 | Bohn et al. . |
| 4,300,544 | 11/1981 | Rudel . |
| 4,304,226 | 12/1981 | Drobish et al. . |
| 4,309,997 | 1/1982 | Donald . |
| 4,317,447 | 3/1982 | Williams ............................ 604/364 |
| 4,332,243 | 6/1982 | Gutnick . |
| 4,349,026 | 9/1982 | Teruo . |
| 4,354,494 | 10/1982 | Hogin . |
| 4,381,771 | 5/1983 | Gabbay . |
| 4,383,993 | 5/1983 | Bawarshi et al. . |
| 4,388,923 | 6/1983 | Heimreid . |

(List continued on next page.)

OTHER PUBLICATIONS

Fawn Vrazo (1992) "In the Works, A Female Condom", *New York Daily News.*

Lawrence K. Altman (Jul. 21, 1992) "Women World-
(List continued on next page.)

*Primary Examiner*—Michael A. Brown
*Attorney, Agent, or Firm*—Kenyon & Kenyon

[57] ABSTRACT

A condom assembly adapted to be received by a passive sexual organ includes a condom and a biocompatible, water soluble, shape-retaining insertion element adapted to deliver the condom to a passive sexual organ, such as the vaginal cavity, prior to intercourse and without first affixing the condom to an erect penis. The assembly may include an applicator to further facilitate insertion of the insertion element housing a condom into the passive sexual organ.

36 Claims, 5 Drawing Sheets

U.S. PATENT DOCUMENTS

| | | | |
|---|---|---|---|
| 4,406,853 | 9/1983 | Teruo . | |
| 4,415,585 | 11/1983 | Joyce et al. . | |
| 4,416,822 | 11/1983 | Campbell . | |
| 4,427,669 | 1/1984 | Blake et al. . | |
| 4,432,357 | 2/1984 | Pomeranz . | |
| 4,439,441 | 3/1984 | Hallesy et al. . | |
| 4,444,789 | 4/1984 | Cormier . | |
| 4,470,996 | 9/1984 | Cormier . | |
| 4,474,769 | 10/1984 | Smith . | |
| 4,475,910 | 10/1984 | Conway et al. . | |
| 4,476,141 | 10/1984 | Cormier . | |
| 4,491,593 | 1/1985 | Gallegos . | |
| 4,493,699 | 1/1985 | Burck et al. . | |
| 4,498,466 | 2/1985 | Pomeranz . | |
| 4,511,558 | 4/1985 | Shur . | |
| 4,527,988 | 7/1985 | Lutz et al. . | |
| 4,530,839 | 7/1985 | Pasquale . | |
| 4,544,554 | 10/1985 | Pasquale . | |
| 4,553,968 | 11/1985 | Komis . | |
| 4,553,972 | 11/1985 | Vickery . | |
| 4,564,006 | 1/1986 | Pomeranz . | |
| 4,564,362 | 1/1986 | Burnhill . | |
| 4,578,219 | 3/1986 | Goldberg et al. . | |
| 4,585,587 | 4/1986 | Goldberg et al. . | |
| 4,590,070 | 5/1986 | Chantler et al. . | |
| 4,601,714 | 7/1986 | Burnhill . | |
| 4,607,474 | 8/1986 | Jarvis . | |
| 4,607,630 | 8/1986 | Spits . | |
| 4,628,051 | 12/1986 | Pasquale . | |
| 4,696,294 | 9/1987 | Reyner . | |
| 4,703,752 | 11/1987 | Gabbay . | |
| 4,711,235 | 12/1987 | Willis . | |
| 4,735,621 | 4/1988 | Hessel . | |
| 4,781,709 | 11/1988 | Grubman . | |
| 4,798,600 | 1/1989 | Meadows . | |
| 4,805,604 | 2/1989 | Spery | 128/844 |
| 4,821,741 | 4/1989 | Mohajer . | |
| 4,834,113 | 5/1989 | Reddy . | |
| 4,834,114 | 5/1989 | Boarman . | |
| 4,840,624 | 6/1989 | Lee . | |
| 4,856,534 | 8/1989 | Sorkin et al. . | |
| 4,867,176 | 9/1989 | Lash | 128/844 |
| 4,873,996 | 10/1989 | Maurer | 128/844 |
| 4,875,490 | 10/1989 | Quiroz | 128/844 |
| 4,898,184 | 2/1990 | Skurkovich et al. . | |
| 4,906,242 | 3/1990 | Thomas . | |
| 4,945,923 | 8/1990 | Evans et al. . | |
| 4,954,530 | 9/1990 | Hidenori et al. . | |
| 4,966,165 | 10/1990 | Anderson . | |
| 4,966,166 | 10/1990 | Leffler . | |
| 4,972,849 | 11/1990 | Park . | |
| 4,976,273 | 12/1990 | Hessel . | |
| 4,993,431 | 2/1991 | Reddy . | |
| 4,993,433 | 2/1991 | Reddy . | |
| 5,046,489 | 9/1991 | Gibson | 128/844 |
| 5,065,771 | 11/1991 | Ferguson . | |
| 5,074,314 | 12/1991 | Wilson . | |
| 5,076,287 | 12/1991 | Johnson . | |
| 5,094,250 | 3/1992 | Hessel . | |
| 5,109,871 | 5/1992 | Thornton . | |
| 5,113,873 | 5/1992 | Boarman . | |
| 5,267,575 | 12/1993 | Hrishko | 128/844 |

OTHER PUBLICATIONS wide Nearing High Rate for Aids Than Men", *The New York Times*, p. C3.

C. G. Gebelein et al. (1985) in *Bioactive Polymeric Systems, An Overview*, pp. 5–6.

M. A. Wainberg et al. *Arch of Aids Res.*, vol. 1, pp. 57–68.

F. Mendez et al. Arch Aids Res., vol. IV, pp. 115–135.

D. Serfaty (1988) *Contraception–Fertilite*, vol. 16(3), pp. 213–220.

R. L. Dunn et al. (1988) *Polymers in Medicine III*, pp. 149–160.

E. H. in "Mirabella, " Aug. 1992, p. 70.

Vaginal Contraceptive Film (VCF), Apothecus Inc.

1988 *Clinca*, vol. 297, p. 20.

(1988) *Clinica*, vol. 298, p. 24.

(1992) "The Gay Men's Health Crisis Newsletter of Experimental Aids Therapies", vol. 6(7), pp. 1–27.

Joe Nicholson in "New York Post," May 21, 1987.

Associated Press, "New York Post," Feb. 25, 1988.

Michael Gross in "The New York Times," Feb. 25, 1987.

(Aug. 1987) "Self" Magazine Condom Confidence: How to Make Them Safer.

(Oct. 1972) "Mademoiselle" Magazine The Female Condom: One Woman's Story.

RECEPTIVE CONDOM ASSEMBLY

This invention relates to the field of contraception and to the control of venereal disease transmission, including Acquired Immune Deficiency Syndrome (AIDS) and Human Immunodeficiency Virus (HIV) infection. In particular, this invention relates to an improved receptive condom assembly for use by a passive sexual partner.

BACKGROUND OF THE INVENTION

Since the discovery of AIDS in 1981, gay men in the urban areas accounted for approximately two-thirds of all AIDS cases in the United States, Europe, and Latin America. This proportion, however, is rapidly changing due to increasing numbers of heterosexual women becoming infected through sexual intercourse with infected men. According to the World Health Organization (WHO), it is anticipated that most new infections will occur in women by the year 2000. See, L. K. Altman "New York Times" Jul. 21, 1992, page C3. With the staggering increase in sexually transmitted diseases such as AIDS, there has been a resurgence of interest toward the development of reliable, convenient contraceptive/prophylactic devices to be worn by a passive sexual partner during sexual relations.

Devices which prevent undesired conception and/or exchange of bodily fluids during sexual intercourse have been known for many years. Female contraceptives are generally divided into four basic types which include orally administered pharmaceuticals; the cervical cap; devices which rely on chemical spermicides, such as diaphragms, sponges, foams, jellies, dermal implants and suppositories; and the intrauterine device. These contraceptives, however, suffer from a number of serious disadvantages.

Although effective in preventing conception, oral contraceptives reportedly have various undesirable side effects, including possible implication in carcinogenic damage to the gall bladder and liver. The diaphragm, while reliable when correctly used, is a cumbersome and inconvenient contraceptive that can easily interrupt or detract from the act of intercourse. Spermicidal contraceptives are also inconvenient to use and may be only as much as 85% reliable as a contraceptive. The cervical cap cannot be fitted on some women, and on women who are able to wear it, it may produce discomfort and infection. The intrauterine device has been the subject of much public controversy and has been reported to be unsafe under certain circumstances.

There may also be a possibility of danger to women who are susceptible to Toxic Shock Syndrome, since the cervical cap, the intrauterine device and spermicidal implants are all foreign bodies that are left inside the vaginal vault either permanently or for several hours after intercourse.

These known methods of female contraception do not provide adequate and independent protection from sexually transmitted diseases. Although spermicidal implants may provide some protection, the available female contraceptives do not provide a reliable impermeable barrier to infection vectors such as HIV.

Unlike female contraceptives, the male condom is the usual form of contraceptive available to men. It is also the most reliable protection against sexually transmitted disease that is currently available to either sex, even though the male condom may have a failure rate as high as 17%. The male condom, especially when made of latex, provides an effective membrane barrier against the transmission of infection. Additionally, the present male condom is widely available, economical, does not require a doctor's services, and does not normally cause any side effects to either partner.

The conventional male condom comprises an elongated tubular sheath made of thin, flexible material such as latex film. The sheath is closed at one end and open at the other end to provide for the insertion of a penis. The opening includes a periphery having a beaded or constricted rim. The condom is put on by rolling it onto or pulling it onto an erect penis. The latex-type condom fits tightly in order to be kept in place during intercourse.

The male condom has several disadvantages which include breakage, leakage, and slippage. After ejaculation, if the penis is left inside and continues to soften, the conventional condom may slip off, causing unwanted leakage of semen and infectious matter. Additionally, the penis must be erect in order to put on the condom, which causes an untimely interruption of the sex act. Furthermore, the loss of sensation experienced by the man may be caused by the fact that the present male condom must often be tight-fitting in order to stay in place. Because of the loss of sensation and inconvenience, men generally consider the use of condoms undesirable and there is often great resistance to their use on a regular basis.

Recent attempts have been made to design a condom or condom-like device as a contraceptive/prophylaxis devices to be worn on the inside of the passive sexual organs of a passive partner. See, U.S. Pat. Nos. 4,805,604; 4,867,176; 4,945,923; 4,976,273; and 5,074,314 for examples of such condom devices. These devices include condoms having a disposable applicators or condoms having built-in retaining elements, e.g. rings, to secure the condom within the passive sexual organ. A sampling of these attempts is described below.

U.S. Pat. No. 4,805,604 describes a receptive condom device adapted to be received by a passive sexual organ prior to intercourse. The device consists of a thin elastic membrane sheath having a closed end, a supporting ring structure at its open end, and an insertion tube adapted to deliver the condom to a passive sexual organ prior to intercourse. A charge of compressed air, in communication with the inside of the condom, forces the condom out of the tube end into the passive sexual organ closed end first. The collapsed charge and insertion tube are then removed, leaving the condom in place. While the condom device is satisfactory for its intended use, the described method of application could be improved.

U.S. Pat. No. 4,867,176 describes a female condom and a disposable tampon-like applicator device adapted to facilitate vaginal insertion. The condom is inserted into the vagina using the applicator fitted with a broad tip portion which is received in the closed distal end of the condom. The applicator is then removed, leaving the condom in place. The disadvantages of the described device is that applicator is cumbersome and may inadvertently rip or tear the condom during insertion into the vagina or pull the condom out from the vagina during removal of the applicator device.

U.S. Pat. No. 5,074,314 describes a protective sheath for use in a bodily orifice containing a inner solid retention element at the closed bottom end for retaining or securing the sheath within the orifice. The disadvantage of the described device is that the retention element may cause physical discomfort for the wearer during sexual relations. Moreover, the protective sheath does not include an applicator to properly align the retention element within the vagina.

U.S. Pat. Nos. 4,945,923 and 4,976,273 describe a vaginal sheath having flexible rings at both the top open and bottom closed ends. The bottom ring portion of the sheath is inserted into the vagina for anchoring against the cervix like a diaphragm. The disadvantages of the described devices are that they are cumbersome and difficult to fit. Moreover, it is also known that such devices are difficult to correctly insert into the vagina. See, for example, E. H. in "Mirabella," August 1992, page 70 and F. Vrazo in "New York Daily News," Jan. 22, 1990.

Accordingly, there is a need in the art for a simple and convenient condom assembly and method of application for a sexually passive partner which overcomes at least some of the aforementioned deficiencies in conventional devices.

SUMMARY OF THE INVENTION

The present invention provides a receptive condom assembly adapted to be worn by the sexually passive partner, e.g., male or female, comprising a condom and an insertion element. The receptive condom assembly may include an optional applicator element. The condom comprises a thin elastic sheath that is closed at one end and open at the other and which has a generally phallic shape. The sheath is sized to fill and line the passive sexual organ of the passive partner, receive a penis at the open end, yield to a penis within the passive sexual organ, and enclose without actively gripping the penis. Within the context of this invention, a passive sexual organ is any organ which receives an erect penis during sexual relations (e.g., intercourse).

In one embodiment of the invention, a sheath having a supporting double ring structure, such as the one described in my prior U.S. Pat. No. 4,805,604, may be used in the condom assembly of the present invention. In this embodiment, the sheath is provided with a cushioning outer ring of soft, smooth rubber at the open end. The outer cushioning ring surrounds a thin, inflexible (but not hard) rubber inner ring, which fits on the outside of the opening of a passive sexual organ. The purpose of the inflexible inner ring is to provide rigidity, so that the soft rubber outer ring does not fold or buckle and get pushed or pulled inside the passive sexual organ during sexual relations. The receptive condom sheath and ring may also be sized for comfort, for example within a range of at least five sizes—petite, small, medium, large, and extra large. The size needed is determined by the size of the opening of the passive sexual organ.

If desired, the double ring structure may encircle and rest around the base of the penis when penetration is completed, forming a barrier against leakage of seminal fluids over the ring and out of the open end of the condom. In some cases, due to the individual size differences, the double ring structure will create a seal around the base of the penis, thereby holding the sheath in place over the penis during sexual relations, without requiring the sheath to fit tightly. The double ring structure, however, prevents the receptive condom from being pushed into the passive sexual organ.

As an improvement over the sheath described in my prior U.S. Pat. No. 4,805,604, the present invention provides a sheath which is attached to and within a cushioning ring at a location midway between the inner and outer circumferences of the cushioning ring. By attaching the sheath to the cushioning ring in this manner, tearing or ripping of sheath away from the ring due to pulling or tugging motions, such as those occurring during insertion of the penis into the sheath and sexual relations, would be reduced or eliminated. If desired, the cushioning ring may be optionally provided with a thin, inflexible (but not hard) rubber inner ring, such as one described in my prior U.S. Pat. No. 4,805,604. Other receptive sheaths or unisex condoms may be used in the condom assembly of the present invention such as the ones described in U.S. Pat. Nos. 4,805,604; 4,945,923 and 4,976,273.

The condom assembly of the present invention includes an insertion element for inserting the condom sheath, closed end first, into the passive sexual organ of a passive partner. The insertion element comprises a shape-retaining insertion housing tube having an open rear end and a front end which may be open or closed. The front end of the insertion tube is adapted to receive the condom closed end first.

The insertion tube comprises a water soluble, shape-retaining film of sufficient rigidity to facilitate insertion of the insertion tube into the passive sexual organ front end first. After insertion, the insertion tube remains within the passive sexual organ and readily dissolves on contact with the moist mucous surface lining of the passive sexual organ to form a liquid or gel. The insertion tube is made from any suitable biocompatible, water soluble, shape-retaining material such as natural or synthetic polymers and should not cause mucous membrane irritation. Suitable, but non-limiting, materials for making the insertion element of the invention include gelatin and gelatin-containing mixtures such as gelatin, polyvinyl alcohol, and glycerin such as described for VCF (Vaginal Contraceptive Film), a female contraceptive film produced by Apothecus, Inc. (New York, USA). A preferred material for use in the invention is gelatin. The insertion tube may also contain bioactive materials such as spermicidal, anti-viral or anti-bacterial agents. Such materials may be incorporated into the insertion tube as a surface coating or may be mixed into the water soluble shape-retaining material. If desired, water or a water-based lubricant may be applied to the outer surface of insertion element as a coating to facilitate insertion of the condom into the passive sexual organ. This coating is applied to the insertion tube just prior to insertion to prevent premature dissolution of the insertion tube.

The condom assembly of the present invention may also include an applicator element. In this embodiment, an assembly of the applicator element, an insertion element, and a condom (discussed above) housed within the insertion element is contemplated. The applicator element comprises an applicator tube having an open rear end adapted to receive and surround a portion of a finger and a closed front end which is adapted to be inserted into the rear open end portion of the insertion tube. The applicator tube, in communication with the finger, confronts the front end portion of the condom and is co-axially aligned with the insertion tube. The applicator tube facilitates the insertion of the insertion tube (front end first) into the passive sexual organ by a piloting motion of the finger and minimizes any threat to the integrity of the condom body by a fingernail during insertion into a passive sexual organ.

The applicator tube is preferably composed of a disposable rigid material such as glazed cardboard or plastic. If desired, the applicator tube (like the insertion tube) may be composed of a biocompatible, water soluble, shape-retaining film such as the one described (above) for the insertion element, and may be left in place within the condom body after insertion into the passive sexual organ.

In another embodiment of the invention, the closed front end of the applicator tube may contain a releasable encapsulated liquid, e.g. spermicide or lubricant, between a thin burstable outer wall and thin flexible inner wall which is adapted to be released into the inner condom surface by finger pressing against the flexible inner wall in front closed end portion of the applicator tube. U.S. Pat. No. 4,332,243, incorporated by reference in its entirety, describes examples of contraceptive devices, e.g. condom, containing encapsulated liquids which are releasable during intercourse.

There are numerous advantages achieved by the receptive condom when compared to conventional condoms and methods of birth control. There is no loss of spontaneity, as the receptive condom can be inserted before foreplay begins. Since the double ring structure remains on the outside of the sexual orifice, with or without gripping the penis, the penis may remain inside and grow soft, with no danger of slipping of the condom or subsequent leakage. The receptive condom may also be left in place for a repeat performance, if desired but repeated usage is generally not recommended. The receptive condom does not have to fit the penis tightly, and therefore loss of sensation is reduced.

Other advantages include an increased responsibility for birth control by the woman. Also, the condom assembly according to the invention is economical and does not require a visit to a clinic or doctor's office.

Protection from sexually transmitted diseases can be improved over the 17% failure rate of the present male condom, because the problems of slipping, falling off, breakage, and leakage may be rectified by the external ring of the invention, by the looser fit, and by the reduced stress which the receptive condom incurs.

The receptive condom may include but does not require the use of chemical spermicides or anti-disease medication. Like conventional condoms, the invention can be removed after intercourse (unlike the sponge or diaphragm, which must be left in for 6 to 8 hours in order to be effective)—a definite advantage to women who are susceptible to Toxic Shock Syndrome or allergic reactions to chemicals.

These and other advantages and objectives of the invention will be apparent from the following description and drawings.

DETAILED DESCRIPTION

All patents and references cited within this specification are hereby incorporated by reference in their entirety.

Figure 1A:
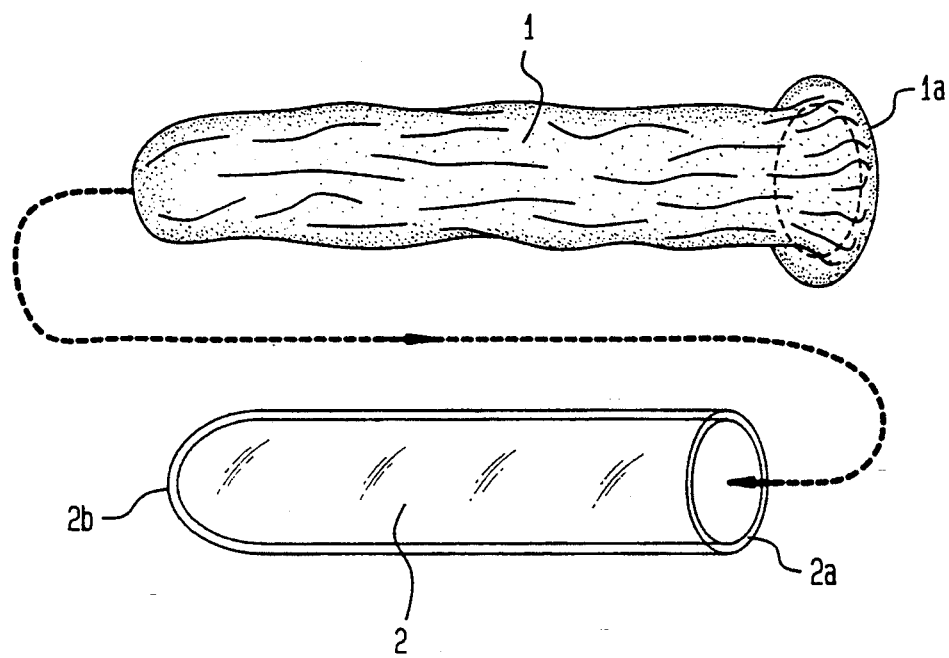
FIG. 1a shows an unassembled receptive condom and an insertion tube 2 having an open rear end 2a and closed front end 2b. The receptive condom comprises a condom body 1 having an open end and a closed end and a circular cushioning 1a ring at the open end.

Referring to FIG. 1, the invention comprises an assembly of a condom body 1 and an insertion element 2. The condom body 1 is generally phallic in shape and is closed at one end and open at the other end. The condom body may be constructed of latex film materials, natural lamb ceca products, or other materials suitable for use as a condom body. The body 1 is larger than that of conventional male condoms so that, when the receptive condom is fully open and extended, it will surround but not actively grip an erect penis.

Figure 2:
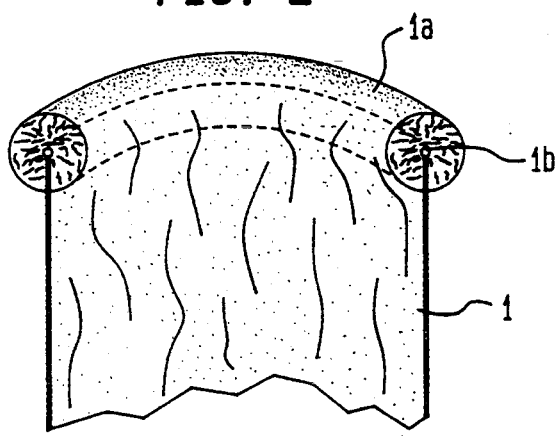
FIG. 2 is a partial cross-sectional view of an improved receptive condom comprising a sheath and a circular cushioning ring wherein the sheath is attached to and within the cushioning ring and is positioned midway between the inner and outer circumference of the ring.

In practicing the invention, any suitable receptive or unisex condom such as the ones described in U.S. Pat. Nos. 4,805,604; 4,945,923 and 4,976,273, may be used in making the condom assembly. In practicing the invention, a preferred condom is one having a cushioning ring 1a affixed to the open end such as the condom described in U.S. Pat. No. 4,805,604. To further strengthen the integrity of condom during sexual relations, the present invention provides an improved receptive condom wherein the condom body 1 is attached at position 1b within the cushioning ring 1a and between the inner and outer diameters of the cushioning ring 1a as shown in FIG. 2. By attaching the sheath to the cushioning ring in this manner, tearing or ripping of the condom body 1 away from the ring 1a due to pulling or tugging motions, such as those occurring during insertion of the penis into the sheath and during sexual relations, would be reduced or eliminated. If desired, the cushioning ring may be optionally provided with a thin, inflexible (but not hard) rubber inner ring, such as one described in U.S. Pat. No. 4,805,604.

Figure 1B:
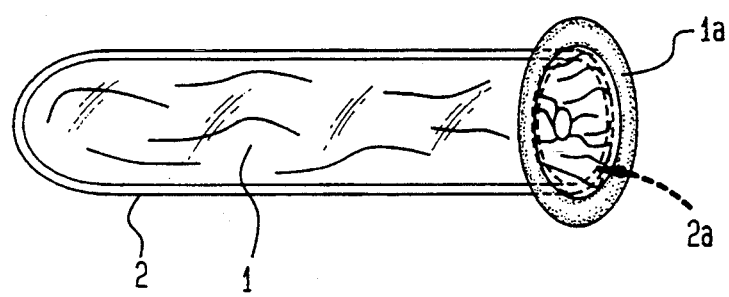
FIG. 1b shows a receptive condom assembly in storage condition wherein the condom body 1 is housed in the insertion tube 2.

As shown in FIG. 1b, the body of the condom 1, before use, is assembled into an insertion element, such as insertion tube 2, which serves to store and house the condom. The condom body 1 is placed closed end first into the open rear portion 2a of insertion tube 2, so that the condom body 1 resides within the insertion tube 2 and the cushioning ring 1a extends outside of the open rear portion 2a of the insertion tube 2. The open end 2a of the insertion tube 2 is adapted to receive a finger or an applicator element.

Figure 3A:
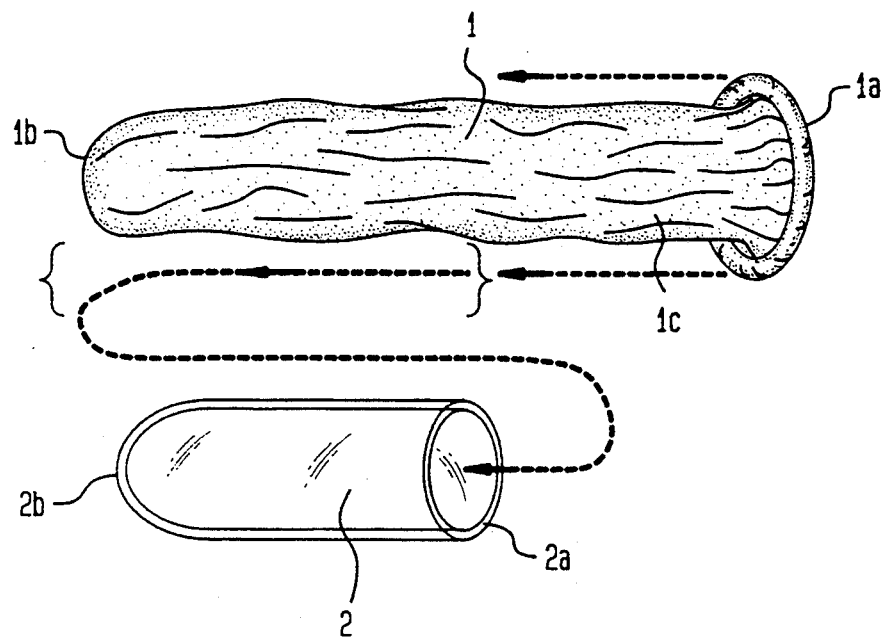
FIG. 3a shows an unassembled receptive condom and an insertion tube 2 having an open rear end 2a and closed front end 2b wherein a portion of the condom body 1 is to be partially inserted into insertion tube 2.
Figure 3B:
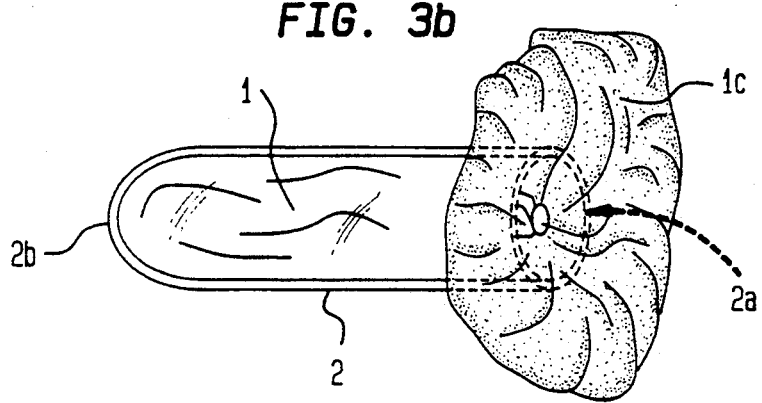
FIG. 3b shows a receptive condom assembly in storage condition wherein a portion of the condom body 1 is housed in the insertion tube 2.

In another embodiment of the condom assembly of the invention as shown in FIGS. 3a and 3b, a rear portion (1c) of the condom body 1 extends outside of the rear portion 2(a) of the insertion tube 2, and is rolled up around the ring 1a. In this embodiment, the condom body 1 is placed closed-end first into the open-ended insertion tube 2, so that a front portion 1(b) of the condom body 1 resides within the insertion tube 2. A rear portion 1(c) of the condom body 1 extends outside the rear portion 2(a) of the insertion tube 2, and is rolled up around ring 1a. FIG. 3b shows a receptive condom assembly having a portion of the condom body 1 housed in insertion tube 2.

Figure 4A:
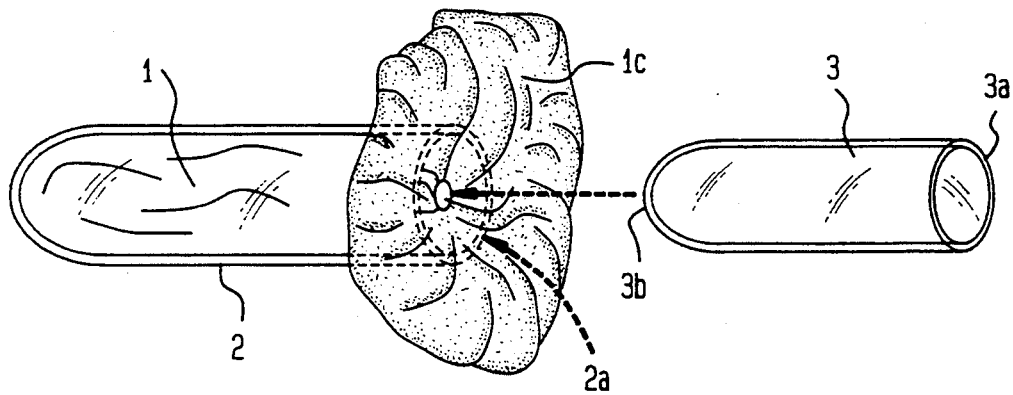
FIG. 4a shows the positioning of an applicator 3 into the receptive condom assembly of FIG. 3b.

FIG. 4a shows positioning of an applicator element such as applicator tube 3 having an open rear end 3(a) adapted for receiving and surrounding a finger and a closed end 3(b) adapted for inserting into the open rear end 2(a) of the inserter tube 2. The applicator tube 3 is in co-axial communication with the insertion tube 2 and confronts the inner surface of the open end of the condom housed in the insertion tube 2.

Figure 4B:
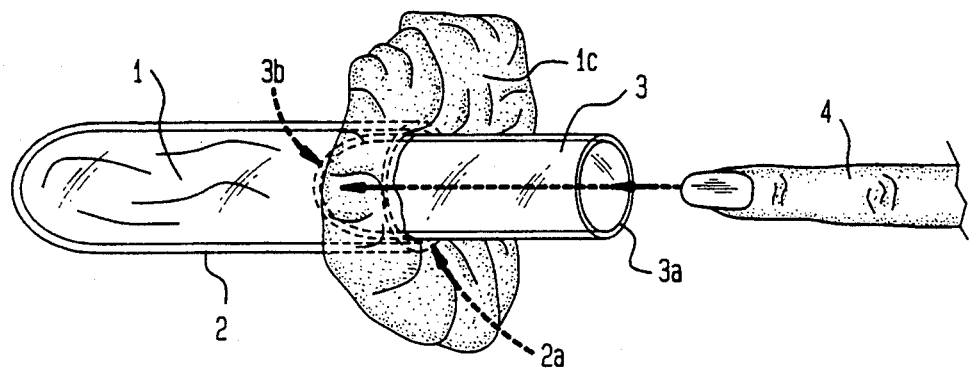
FIG. 4b illustrates a receptive condom assembly having an applicator and shows the interaction between the applicator 3 and a finger 4.

The diameter of the open rear end portion 2(a) of insertion tube 2 should be slightly larger than that of the closed front end portion 3(b) of the applicator tube 3 so as to receive and surround the front closed end 3(b) portion of applicator tube 3. The diameter of applicator tube 3 should be sufficient to accommodate a portion of an average adult finger at least partially, preferably completely. FIG. 4b shows a receptive condom assembly of an insertion tube 2, the condom body 1 and an applicator 3. This Figure also illustrates the insertion of a finger 4 into the open end 3(a) portion of applicator 3.

Figure 5A:
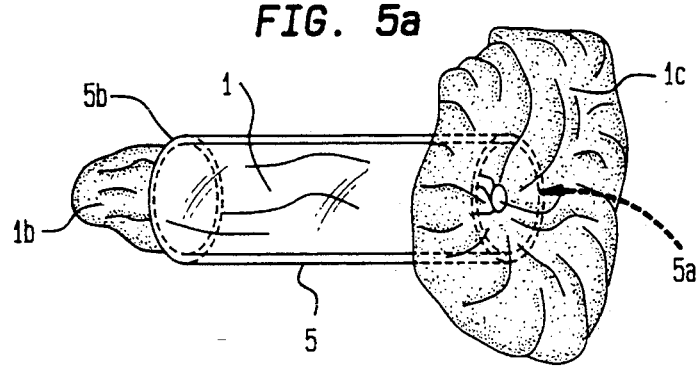
FIG. 5a illustrates a receptive condom assembly having an open-ended insertion tube and an applicator.

In another embodiment of the invention as shown in FIG. 5a, a receptive condom assembly is shown wherein condom body 1 is housed in a insertion tube 5 having an open front end 5(b) and an open rear end 5(a). The condom body 1 is placed into the open ended tube 5 so that a front portion 1(b) of condom body 1 extends from the front end portion 5(b) of the insertion tube and the rear portion 1(c) extends outside of open rear end 5(a) of the insertion tube. Portion 1(a) of the condom body 1 may be positioned within insertion tube 5 (not shown). If desired, the entire condom body 1 may be housed in insertion tube 5 with the cushioning ring 1a extending outside of the rear open end 5a (not shown) of the insertion tube 5 in a manner similar to FIG. 1b.

Figure 5B:
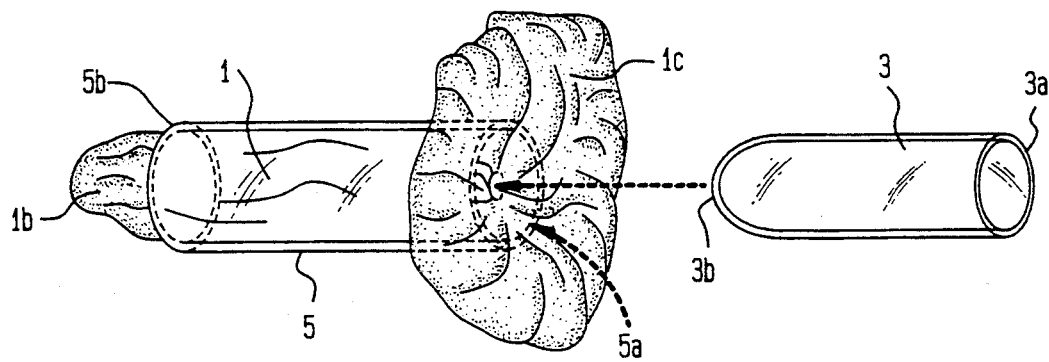
FIG. 5b shows the positioning of an applicator 3 into a receptive condom assembly.
Figure 5C:
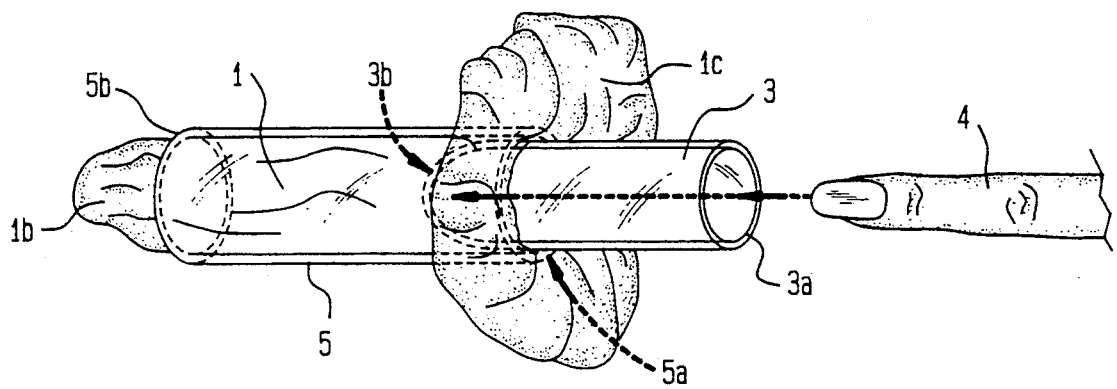
FIG. 5c illustrates a receptive condom assembly having an applicator and shows the interaction between the applicator tube and a finger.

FIG. 5b shows positioning of an applicator element such as applicator tube 3 having a closed front end 3(b) portion adapted for insertion into the receptive condom assembly. The applicator tube 3 is in co-axial communication with the insertion tube 5 and confronts the inner surface of the open end of the condom housed in the insertion tube 5 in the same manner shown in FIG. 4a. FIG. 5c shows a receptive condom assembly of an insertion tube 5, the condom body 1, and applicator 3. This Figure also illustrates the insertion of a finger 4 into the open end portion 3(a) of applicator 3.

Figure 6:
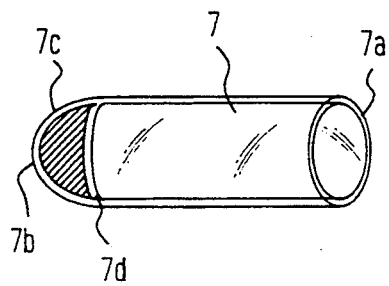
FIG. 6 shows an applicator having entrapped or encapsulated liquid at the closed end of the tube.

FIG. 6 illustrates another embodiment of an applicator element. In this embodiment, the closed front end of an applicator tube 7 contains an encapsulated liquid 7(c) between a thin burstable wall 7(b) and a flexible inner wall 7(d). The encapsulated liquid composition 7(c) is released, e.g. by bursting, into the inner surface of front portion of the condom body 1 (not shown) housed in an insertion element such as the assemblies shown in FIG. 1b, 3b, and 5a. The piloting motion of a finger 4 (shown in FIGS. 4b and 5c) into the applicator tube 7 exerts a pressure against the inner wall 7(d) of the applicator and bursts wall 7(b), thus releasing the encapsulated liquid into the inner surface of open end portion of the condom during insertion into a passive sexual organ. Suitable liquid compositions for use in the invention include lubricants and spermicides such as nonoxinol-9 and octoxynol, and benzalkonium chloride. See, for example, M. A. Wainberg et al. Arch. AIDS Res., Vol. 1, pages 57–68 and F. Mendez et al., ibid, Vol. 4, pages 115–135.

Figure 7:
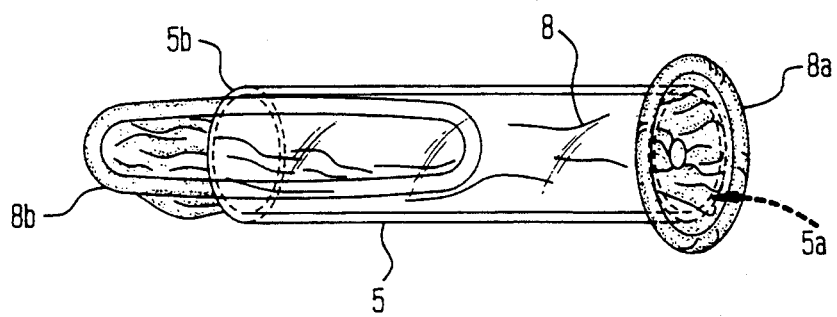
FIG. 7 illustrates a receptive condom assembly for a condom having a ring at the open end and closed end.

FIG. 7 shows another embodiment of the receptive condom assembly of the present invention. In this embodiment, a condom body 8 having a thin flexible ring at the closed end 8(b) and a ring, e.g. a thin flexible ring or cushioning ring, at the open end 8(a) may be delivered into a passive sexual organ, e.g. vagina, by positioning the condom body 8 into an insertion element of the invention, such as an open-end insertion tube 5, so that the ring at position 8(b) of condom body 8 is partially enclosed in the front open end 5(b) of the insertion tube and the ring in position 8(a) extends from the open rear end 5(a) of the insertion tube. If desired, an applicator tube (not shown) may be included as part of the receptive condom assembly.

FIGS. 8(a-c) illustrates the insertion of the receptive condom assembly into a passive sexual organ, e.g. vagina.

Figure 8A:
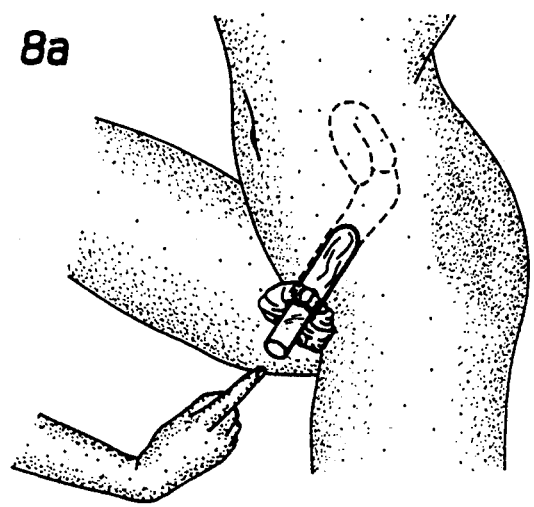
FIGS. 8 (a–c) illustrate the insertion of a receptive condom assembly having an applicator into a passive sexual organ.
Figure 8B:
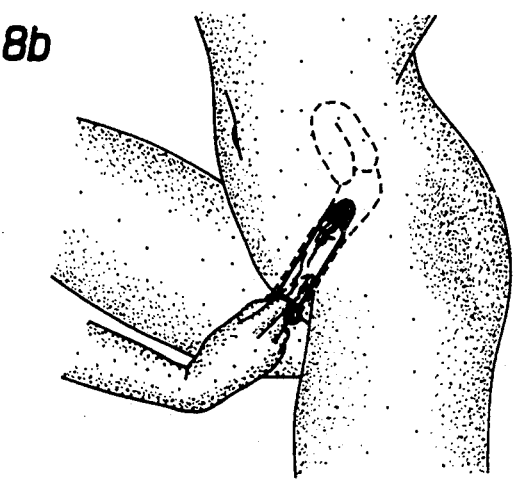
Figure 8C:
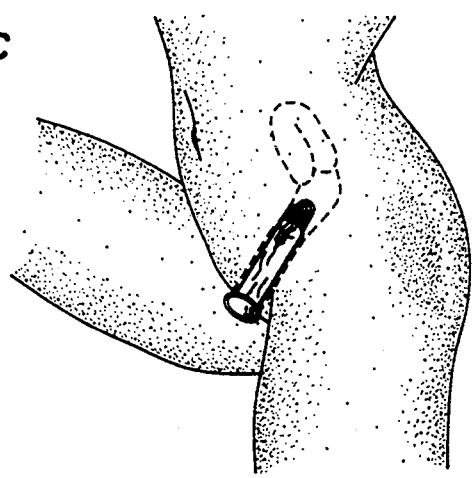

First, a condom assembly such as the one shown in FIG. 4b is inserted into the opening of a passive sexual organ closed-end first, until the cushioning ring 1a prevents any further forward motion, FIG. 8a. Thus, the cushioning ring 1a is always on the outside of the passive sexual organ. Next, a finger inserted into the rear open end 3(a) of applicator 3 is used to pilot the condom body 1 housed in insertion tube 2, so that the entire condom body 1 is inside the passive sexual organ, while the rear portion 1(c) of the condom body 1 continues to surround the front portion 2(a) of the insertion tube 2, FIG. 8b. Finally, as shown in FIG. 8c, the applicator tube 3 is removed (not shown), leaving the receptive condom 1 and insertion tube 2 in place inside a passive sexual organ, prior to receiving a penis.

The preferred applicator is an applicator tube having a closed front end and a open rear end. Other suitable applicator elements could also be used, such as the mechanical plunger described in U.S. Pat. No. 4,867,176. In theory, an applicator tube having a closed end is preferred, because it poses less of a threat to the integrity of the condom body due to accidental finger nail puncture and provides a more convenient "one-step" application.

The insertion element of the present invention may also be used to deliver agents into a bodily orifice, e.g. vagina or rectum. Suitable, but non-limiting, agents include spermicides, lubricants, and medicaments for treating infections or irritations. These agents may be carried within the insertion element or may be physically affixed to the insertion element, e.g. an insertion tube, as a surface coating or by comminution with the biocompatible water soluble polymer used in making the insertion element. Preferably, the agents are in powdered or dried form to prevent dissolution of the insertion element during storage. Alternatively, if solutions or suspensions of the agents are used, these may be placed into the insertion tube just prior to insertion into the bodily orifice. In the preferred embodiment of the invention, an assembly for delivering the agent into a bodily orifice is provided and which includes the insertion element and an applicator such as the ones described above.

The receptive condom assembly of the present invention, with or without an applicator, may be individually packaged and stored in conventional tamper-proof sanitary packaging means for future use.

What is claimed is:

1. An assembly for delivering a condom into a passive sexual organ comprising:
   a condom; and
   an inserter comprising a biocompatible, water soluble, shape-retaining insertion tube having an open front end and a housing portion, adapted for housing said condom, extending from said open front end.

2. The assembly of claim 1, wherein said insertion tube is comprised of gelatin.

3. The assembly of claim 1, wherein said open front end is adapted for receiving an applicator.

4. The assembly of claim 1, wherein the insertion tube has a rear open end.

5. The assembly of claim 1, wherein the condom is adapted to be received by a passive sexual organ.

6. An assembly for delivering a condom into a passive sexual organ comprising:
   an elastic sheath having a closed end, an open end, and a generally phallic shape, said sheath being adapted to receive a male sexual organ via the open end; and
   an inserter comprising a biocompatible, water soluble, shape-retaining insertion tube having an open front end and a housing portion extending from said open front end of said tube and surrounding a portion of said sheath extending from said closed end of said sheath.

7. The assembly of claim 6, wherein the insertion tube is comprised of gelatin.

8. The assembly of claim 6, wherein the insertion tube has a rear open end.

9. The assembly of claim 6, wherein said sheath is comprised of thin uniform elastic material and is sized to receive and enclose, without actively gripping, a male sexual organ.

10. The condom assembly of claim 6, wherein the length of said insertion tube is less than the length of said sheath.

11. The assembly of claim 6 additionally comprising an applicator for piloting said sheath into the passive sexual organ, the applicator being in co-axial communication with the insertion tube and confronting a portion of the sheath.

12. The assembly of claim 11, wherein said applicator comprises an applicator tube having a closed end adapted for receiving the open front end of said insertion tube and a rear open end adapted for receiving a finger.

13. The condom assembly of claim 12, wherein said closed end of said applicator tube contains a burstable wall and a flexible wall, said burstable wall and said flexible wall enclosing a liquid.

14. The condom assembly of claim 11, wherein said applicator is comprised of a biocompatible, water-soluble, shape-retaining material.

15. The assembly of claim 11, wherein said applicator is comprised of gelatin.

16. An assembly for delivering a condom into a passive sexual organ comprising:
   an elastic sheath having a closed end, an open end, and a generally phallic shape, said sheath being adapted to receive a male sexual organ via the open end; and
   a biocompatible, water soluble, shape-retaining insertion tube having an open front end and a housing portion extending from said open front end of said tube and surrounding a portion of said sheath extending from said closed end of said sheath.
   an applicator in coaxial communication with said insertion tube and confronting a portion of said sheath.

17. The assembly of claim 16, wherein said applicator comprises an applicator tube having a closed end adapted for receiving the open front end of said insertion tube and a rear open end adapted for receiving a finger.

18. The condom assembly of claim 17, wherein said closed end of said applicator tube contains a burstable wall and a flexible wall, said burstable wall and said flexible wall enclosing a liquid.

19. The condom assembly of claim 16, wherein said applicator is comprised of a biocompatible, water soluble, shape-retaining material.

20. The assembly of claim 16, wherein said applicator is comprised of gelatin.

21. The assembly of claim 16, wherein the insertion tube is comprised of gelatin.

22. The assembly of claim 16, wherein the insertion tube has a rear open end.

23. The assembly of claim 16, wherein said sheath is comprised of a thin uniform elastic material and is sized to receive and enclose, without actively gripping, a male sexual organ.

24. An assembly for delivering a condom into a passive sexual organ comprising:
   an elastic sheath having a closed end, an open end, and a generally phallic shape, said sheath being adapted to receive a male sexual organ via the open end; and said sheath having a front portion proximate to said closed end and a rear portion proximate to said open end,
   an outer flexible ring circumferentially affixed to the open end of said sheath, said outer ring containing a thin, inflexible inner ring within and attached to said outer ring, the two ring combination having an internal diameter adapted to receive and guide the male sexual organ into said sheath without actively gripping said male sexual organ, and
   an inserter comprising a biocompatible, water soluble, shape-retaining insertion tube having an open front end and a housing portion extending from said open front end of said tube and surrounding a portion of said sheath extending from said closed end of said sheath.

25. The assembly of claim 24 additionally comprising an applicator for piloting said sheath into the passive sexual organ.

26. The assembly of claim 25, wherein said applicator comprises an applicator tube having a closed end adapted for receiving the open front end of said insertion tube and a rear open end adapted for receiving a finger.

27. The condom assembly of claim 26, wherein said closed end of said applicator tube contains a burstable wall and a flexible wall, said burstable wall and said flexible wall enclosing a liquid.

28. The condom assembly of claim 25, wherein said applicator is comprised of a biocompatible, water soluble, shape-retaining material.

29. The condom assembly of claim 25, wherein said applicator is comprised of gelatin.

30. The assembly of claim 24, wherein said insertion tube is comprised of gelatin.

31. The assembly of claim 24, wherein said sheath is comprised of thin uniform elastic material and is sized to receive and enclose, without actively gripping, a male sexual organ.

32. The condom assembly of claim 24, wherein said sheath is made from a material selected from the group consisting of latex film materials and natural lamb cecum products, said outer ring is made of a soft flexible material, and said inner ring is made of a thin, inflexible material.

33. An assembly for delivering a condom adapted to be worn by a sexually passive partner into a passive sexual organ, comprising
 a biocompatible, water soluble, shape retaining insertion tube having an open front end and a housing portion adapted for housing the condom and extending from the open front end of the tube;
 and an applicator for piloting the condom housed in the insertion tube into the passive sexual organ, the applicator being in co-axial communication with the insertion tube and confronting a portion of the condom.

34. The assembly of claim 33, wherein said applicator comprises an applicator tube having a closed end adapted for receiving the open front end of said insertion tube and a rear open end adapted for receiving a finger, and said closed end of said applicator tube contains a burstable wall and a flexible wall, said burstable wall and said flexible wall enclosing a liquid.

35. The assembly of claim 33, wherein said applicator is made of a biocompatible, water soluble, shape retaining material.

36. The condom assembly of claim 33, wherein said applicator is comprised of gelatin.

* * * * *